(12) United States Patent
Koh et al.

(10) Patent No.: US 10,930,859 B2
(45) Date of Patent: Feb. 23, 2021

(54) PHENANTHROQUINAZOLINE-CORE COMPOUNDS

(71) Applicants: Dow Global Technologies LLC, Midland, MI (US); Rohm and Haas Electronic Materials Korea Ltd., Chungcheongnam-do (KR)

(72) Inventors: Kyoung Moo Koh, Midland, MI (US); Mark E. Ondari, Midland, MI (US); Sukrit Mukhopadhyay, Midland, MI (US); Timothy J. Gallagher, Midland, MI (US); Hong-Yeop Na, Chungcheongnam-do (KR)

(73) Assignees: Dow Global Technologies LLC, Midland, MI (US); Rohm and Haas Electronic Materials Korea Ltd., Chungcheongnam-do (KR)

( * ) Notice: Subject to any disclaimer, the term of this patent is extended or adjusted under 35 U.S.C. 154(b) by 338 days.

(21) Appl. No.: 16/086,204

(22) PCT Filed: Mar. 15, 2017

(86) PCT No.: PCT/US2017/022406
§ 371 (c)(1),
(2) Date: Sep. 18, 2018

(87) PCT Pub. No.: WO2017/160905
PCT Pub. Date: Sep. 21, 2017

(65) Prior Publication Data
US 2020/0303659 A1 Sep. 24, 2020

Related U.S. Application Data

(60) Provisional application No. 62/310,202, filed on Mar. 18, 2016.

(51) Int. Cl.
*H01L 51/00* (2006.01)
*C07D 239/74* (2006.01)
*H01L 51/50* (2006.01)

(52) U.S. Cl.
CPC ........ *H01L 51/0072* (2013.01); *C07D 239/74* (2013.01); *H01L 51/5072* (2013.01); *H01L 2251/552* (2013.01); *H01L 2251/556* (2013.01)

(58) Field of Classification Search
CPC ............... H01L 51/0052; H01L 51/006; H01L 51/0067; H01L 51/0072; C07D 239/74
See application file for complete search history.

(56) References Cited

U.S. PATENT DOCUMENTS

2013/0324771 A1 12/2013 Yamada et al.
2015/0364705 A1 12/2015 Jun et al.

OTHER PUBLICATIONS

International Search Report dated Jun. 13, 2017 cited in corresponding PCT Application No. PCT/US2017/022406.

*Primary Examiner* — Anthony Ho
(74) *Attorney, Agent, or Firm* — Mintz Levin Cohn Ferris Glovsky and Popeo, P.C.; Peter F. Corless

(57) ABSTRACT

Provided is a composition comprising one or more phenanthroquinazoline-core compounds having structure (I)

(Continued)

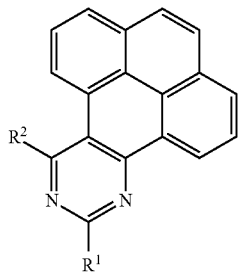 (I)
wherein each of $R^1$ and $R^2$ is independently a substituted or unsubstituted phenyl group.
6 Claims, 1 Drawing Sheet

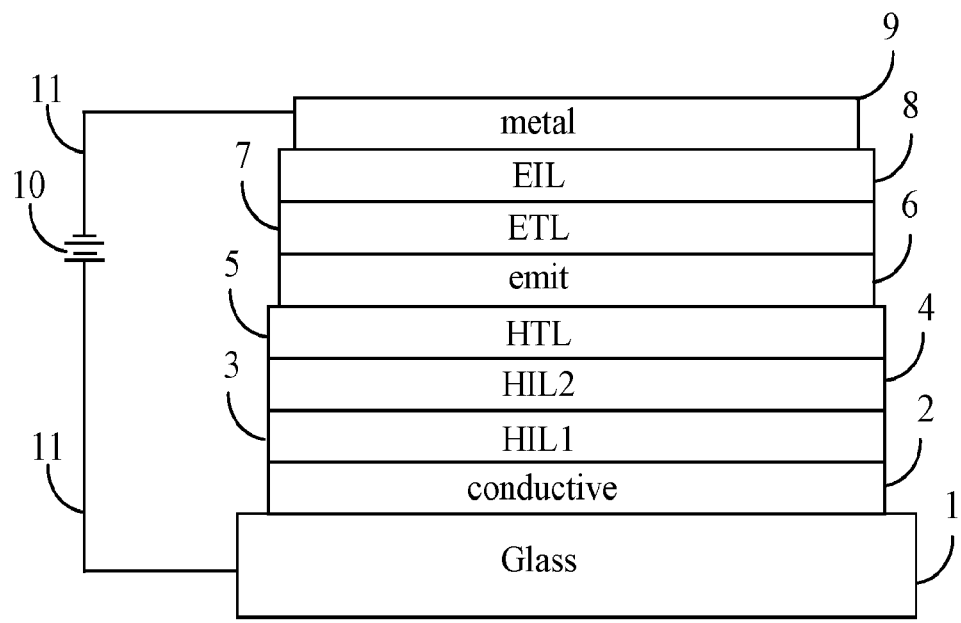

PHENANTHROQUINAZOLINE-CORE COMPOUNDS

CROSS-REFERENCE TO RELATED APPLICATION

This application is a 35 U.S.C.§ 371 U.S. national entry of International Application PCT/US2017/022406, having an international filing date of Mar. 15, 2017, which claims under 35 U.S.C. § 119 the benefit of U.S. Provisional Application No. 62/310,202 filed on Mar. 18, 2016, which is incorporated herein by reference in its entirety. The contents of the foregoing applications are incorporated herein by reference in their entirety.

Many opto-electronic devices are multilayer compositions. For example, organic light-emitting diodes (OLEDs) normally contain multiple layers, including, among other layers, an emitting layer and an electron transport layer (ETL). It is desirable that a compound used in an ETL has one or more of the following characteristics: an non-crystalline structure with a relatively high glass transition temperature; and/or a lowest unoccupied molecular orbital (LUMO) that matches or nearly matches the LUMO of the material in the emissive layer. In order to match common useful emissive layers, it is desirable that the compound in the ETL have LUMO of −1.9 to −1.5 eV.

WO 2007/004799 describes a material for use in a layer of an electronic device, where the material has the structure

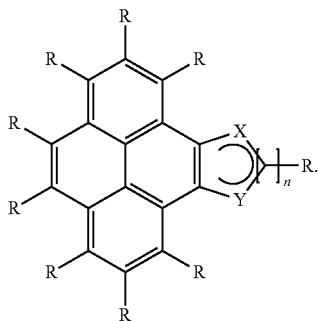

It is desired to provide a composition having improvements in one or more of the characteristics discussed above. It is envisioned that such a composition, if it contained appropriate doping materials, may also be useful in other layers of an opto-electronic device such as, for example, a hole transport layer.

The following is a statement of the invention.

A first aspect of the present invention is a composition comprising one or more phenanthroquinazoline-core compounds having structure (I)

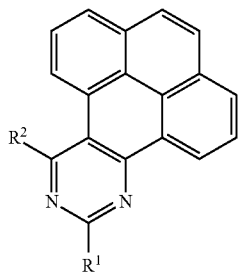

(I)

wherein each of $R^1$ and $R^2$ is independently a substituted or unsubstituted phenyl group.

A second aspect of the present invention is an organic light-emitting diode comprising an emitting layer and an electron transport layer, wherein the electron transport layer comprises the composition of the first aspect.

The following is a brief description of the drawing.

FIG. 1 shows one embodiment of an OLED made using a composition of the present invention.

The following is a detailed description of the invention.

As used herein, the following terms have the designated definitions, unless the context clearly indicates otherwise.

The term "alkoxy," as described herein, refers to an alkyl in which at least one hydrogen atom is substituted with an oxygen atom, O.

The term "alkyl," as described herein, refers to an organic radical derived from an alkyl hydrocarbon by deleting one hydrogen atom therefrom. An alkyl group may be a linear, branched, cyclic or a combination thereof. The term "substituted alkyl," as used herein, refers to an alkyl, in which at least one hydrogen atom is substituted with a substituent that comprises at least one heteroatom. Heteroatoms include, but are not limited to, O, N, P and S. Substituents include, but are not limited to, halide, OR', NR'$_2$, PR'$_2$, P(=O)R'$_2$, SiR'$_3$; where each R' is independently a $C_1$-$C_{20}$ hydrocarbyl group.

The "anode" injects holes into a layer located on the emitting layer side, such as the hole injection layer, the hole transport layer, or the emitting layer. The anode is disposed on a substrate. The anode is typically made from a metal, a metal oxide, a metal halide, an electroconductive polymer, and combinations thereof.

The term "aryl," as described herein, refers to an organic radical derived from aromatic hydrocarbon by deleting one hydrogen atom therefrom. An aryl group may be a monocyclic and/or fused ring system, each ring of which suitably contains from 5 to 7, preferably from 5 or 6 atoms. Structures wherein two or more aryl groups are combined through single bond(s) are also included. Specific examples include, but are not limited to, phenyl, tolyl, naphthyl, biphenyl, anthryl, indenyl, fluorenyl, benzofluorenyl, phenanthryl, triphenylenyl, pyrenyl, perylenyl, chrysenyl, naphtacenyl, fluoranthenyl and the like. The naphthyl may be 1-naphthyl or 2-naphthyl, the anthryl may be 1-anthryl, 2-anthryl or 9-anthryl, and the fluorenyl may be any one of 1-fluorenyl, 2-fluorenyl, 3-fluorenyl, 4-fluorenyl and 9-fluorenyl. The term "substituted aryl," as used herein, refers to an aryl, in which at least one hydrogen atom is substituted with a substituent comprising at least one heteroatom, and any combination thereof. Heteroatoms include, but are not limited to, O, N, P and S. Substituents include, but are not limited to, halide, OR', NR'$_2$, PR'$_2$, P(=O)R'$_2$, SiR'$_3$; where each R' is independently a $C_1$-$C_{20}$ hydrocarbyl group.

The term "aryloxy," as described herein, refers to an aryl in which at least one hydrogen atom is replaced with an oxygen atom, O.

The term "amine" as described herein refers to a compound having one or more amine nitrogen atoms. An amine nitrogen atom is a nitrogen atom that is part of a structure $R^{11}NH_2$, $R^{11}R^{12}NH$, or $R^{11}R^{12}R^{13}N$, where each of $R^{11}$, $R^{12}$, and $R^{13}$ is a substituted or unsubstituted alkyl or aryl group. $R^{11}$, $R^{12}$, and $R^{13}$ may be separate groups, or any two or more of $R^{11}$, $R^{12}$, and $R^{13}$ may be connected to each other to form one or more aromatic ring or one or more aliphatic ring or a combination thereof. An amine may have exactly one amine nitrogen atom or may have two or more amine nitrogen atoms. An amine having one or more aromatic rings is an aromatic amine.

The "cathode" injects electrons into a layer located on the emitting layer side (that is, the electron injection layer, electron transport layer, or the emitting layer). The cathode is typically made from a metal, a metal oxide, a metal halide, an electroconductive polymer, or a combination thereof.

"Dopant" and like terms, refer to a material that undergoes radiative emission from an excited state. The excited state can be generated, for example, by application of electrical current in an electroluminescent device or by energy transfer from the excited state of another molecule.

"Electron injection layer," or "EIL," and like terms is a layer for efficiently injecting electrons injected from the cathode into the electron transport layer.

"Electron transport layer," or "ETL," and like terms is a layer disposed between the emitting layer and the electron injection layer for improving the luminescent efficiency of the OLED. When placed in an electric field, the electron transport layer transports electrons injected from the cathode toward the emitting layer. The material or composition of the ETL typically has a high electron mobility for efficiently transporting injected electrons.

"Electron Volt" or "eV" is the amount of energy gained (or lost) by the charge of a single electron moved across an electric potential difference of one volt.

"Emitting layer" and like terms, is a layer located between electrodes (anode and cathode) and when placed in an electric field is excited by the recombination of holes injected from the anode through the hole injection layer with electrons injected from the cathode through the electron transport layer, the emitting layer being the primary light-emitting source. The emitting layer consists of host and dopant. The host material could be bipolar or unipolar, and may be used alone or by combination of two or more host materials. The opto-electrical properties of the host material may differ to which type of dopant (Phosphorescent or Fluorescent) is used. For Fluorescent dopants, the assisting host materials should have good spectral overlap between absorption of the dopant and emission of the host to induce good Forster transfer to dopants. For phosphorescent dopants, the assisting host materials should have high triplet energies to confine triplets of the dopant.

"Glass transition temperature" (Tg) as used herein is the temperature of transition of an amorphous solid from a glassy state to a rubbery state. Glass transition temperature is measured at a scan rate of 10° C./min and determined using the "mid-point of inflection" methodology.

The term "heteroalkyl," as described herein, refers to an alkyl group, in which at least one carbon atom or CH group or $CH_2$ is substituted with a heteroatom or a chemical group containing at least one heteroatom. Heteroatoms include, but are not limited to, O, N, P and S. A heteroalkyl group may be a linear, branched, cyclic or a combination thereof. The term "substituted heteroalkyl," as used herein, refers to an heteroalkyl, in which at least one hydrogen atom is substituted with a substituent that comprises at least one heteroatom. Heteroatoms include, but are not limited to, O, N, P and S. Substituents include, but are not limited to, halide, OR", NR"$_2$, PR"$_2$, P($=$O)R"$_2$, SiR"$_3$; where each R" is independently a $C_1$-$C_{20}$ hydrocarbyl group.

The term "heteroaryl," as described herein, refers to an aryl group, in which at least one carbon atom or CH group or $CH_2$ of an aromatic ring is replaced with a heteroatom or a chemical group containing at least one heteroatom. Heteroatoms include, but are not limited to, O, N, P and S. The heteroaryl may be a 5- or 6-membered monocyclic heteroaryl or a polycyclic heteroaryl which is fused with one or more benzene ring(s), and may be partially saturated. The structures having one or more heteroaryl group(s) bonded through a single bond are also included. The heteroaryl groups may include divalent aryl groups of which the heteroatoms are oxidized or quarternized to form N-oxides, quaternary salts, or the like. Specific examples include, but are not limited to, monocyclic heteroaryl groups, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl; polycyclic heteroaryl groups, such as benzofuranyl, fluoreno[4, 3-b]benzofuranyl, benzothiophenyl, fluoreno[4, 3-b]benzothiophenyl, isobenzofuranyl, benzimidazolyl, benzothiazolyl, benzisothiazolyl, benzisoxazolyl, benzoxazolyl, isoindolyl, indolyl, indazolyl, benzothia-diazolyl, quinolyl, isoquinolyl, cinnolinyl, quinazolinyl, quinoxalinyl, carbazolyl, phenanthridinyl and benzodioxolyl; and corresponding N-oxides (for example, pyridyl N-oxide, quinolyl N-oxide) and quaternary salts thereof. The term "substituted heteroaryl," as used herein, refers to a heteroaryl in which at least one hydrogen atom is substituted with a substituent composed of an unsubstituted alkyl, a substituted alkyl, at least one heteroatom, and any combination thereof. Heteroatoms include, but are not limited to, O, N, P and S. Substituents include, but are not limited to, halide, OR', NR'$_2$, PR'$_2$, P($=$O)R'$_2$, SiR'$_3$; where each R' is independently a $C_1$-$C_{20}$ hydrocarbyl group.

A "heteroatom" is an atom other than carbon or hydrogen. Nonlimiting examples of heteroatoms include: F, Cl, Br, N, O, P, B, S, Si, Sb, Al, Sn, As, Se and Ge.

"Hole injection layer," or "HIL," and like terms, is a layer which transports holes from the anode to the emitting layer. The hole injection layer is typically formed on the anode.

"Hole transport layer (or "HTL")," and like terms, refers to a layer made from a material, which transports holes. High hole mobility is recommended for OLED devices. The HTL is used to help block passage of electrons transported by the emitting layer. Small electron affinity is typically required to block electrons. The HTL should desirably have larger triplets to block exciton migrations from an adjacent EML layer.

The term "hydrocarbon," as used herein, refers to a chemical group containing only hydrogen atoms and carbon atoms. The term "hydrocarbon" includes "a hydrocarbyl"" which is a hydrocarbon substituent having a valence (typically univalent). The term "substituted hydrocarbon," (or "substituted hydrocarbyl"), as used herein, refers to a hydrocarbon (or hydrocarbyl) in which at least one hydrogen atom is substituted with a substituent comprising at least one heteroatom. Heteroatoms include, but are not limited to, a halide, O, N, P and S. An "unsubstituted hydrocarbon" (or "unsubstituted hydrocarbyl") is a hydrocarbon that contains no heteroatoms.

The term "independently," or "each is independently selected from," or like terms refers to the separate selection of an element for each individual member within a target group.

The term "nitrile" as used herein refers to a compound having a nitrile group, which is

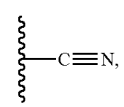

where the jagged line denotes the point of attachment of the nitrile group to the remainder of the molecule.

The term "phenyl group" means a group that has structure (II):

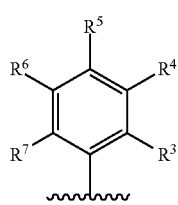
(II)

A phenyl group has a single point of attachment to another molecule. The point of attachment is denoted in groups chemical structures herein by the jagged line symbol ⁀⁀⁀. In an "unsubstituted phenyl group," each of R3 through R7 is hydrogen. In a "substituted phenyl group," one or more of R3 through R7 is an atom or group other than hydrogen. Each of $R^3$ through $R^7$ is independently hydrogen or a substituted or unsubstituted hydrocarbyl group. Any two or more of $R^3$ through $R^7$ may be connected to each other to form a ring structure, which may be aliphatic, aromatic, or a combination thereof, and which may contain a single ring or multiple rings. Each of $R^3$ through $R^7$ optionally contains one or more heteroatom other than carbon and hydrogen.

A "ring structure," as used herein, is a chemical group that contains three or more atoms covalently bonded to each other in such a way that at least one path can be traced along covalent bonds from a first atom, through two or more other atoms, and back to the first atom. A ring structure may contain carbon, hydrogen, one or more atoms other than carbon and hydrogen, or a combination thereof. A ring structure can be saturated or unsaturated, including aromatic, and the ring structure can contain one, or two, or more than two rings.

The "substrate" is a support for the organic light-emitting device. Nonlimiting examples of material suitable for the substrate include quartz plate, glass plate, metal plate, metal foil, plastic film from polymeric resins such as polyester, polymethacrylate, polycarbonate, and polysulfone.

Molecular orbital properties are defined by calculations as follows. The calculations were performed with the hybrid density functional theory (DFT) method, B3LYP, (as described in Becke, A. D. *J. Chem. Phys.* 1993, 98, 5648; Lee, C. et al., *Phys. Rev B* 1988, 37, 785; and Miehlich, B. et al. *Chem. Phys. Lett.* 1989, 157, 200) and the 6-31G* (5d) basis set (as described in Ditchfield, R. et al., *J. Chem. Phys.* 1971, 54, 724; Hehre, W. J. et al., *J. Chem. Phys.* 1972, 56, 2257; and Gordon, M. S. *Chem. Phys. Lett.* 1980, 76, 163). The singlet state calculations used the closed shell approximation, and the triplet state calculations used the open shell approximation. All values are quoted in electronvolts (eV). The highest occupied molecular orbital (HOMO) and the lowest unoccupied molecular orbital (LUMO) values were determined from the orbital energies of the optimized geometry of the singlet ground state. The triplet energies were determined as the difference between the total energy of the optimized triplet state and the optimized singlet state. "HOMO−1" is the energy of the energy state immediately below the HOMO. "LUMO+1" is the energy of the energy state immediately above the LUMO. ΔLUMO+1 is the difference between LUMO+1 and LUMO. T1 is the triplet energy. "λ−" is the reorganization energy for electron transport. Lower λ− leads to higher mobility of electrons through the ETL.

The composition of the present invention contains compound (I):

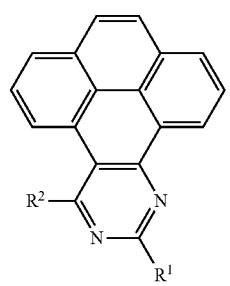
(I)

where each of $R^1$ and $R^2$ is independently a substituted or unsubstituted phenyl group. Preferably, one or both of $R^1$ and $R^2$ contain two or more aromatic rings; more preferably one or both of $R^1$ and $R^2$ contain two or more six-membered aromatic rings in which all six members are carbon atoms.

Preferred $R^1$ and $R^2$ are each independently selected from the following groups, where the jagged line represents the attachment point of the group to the remainder of the molecule:

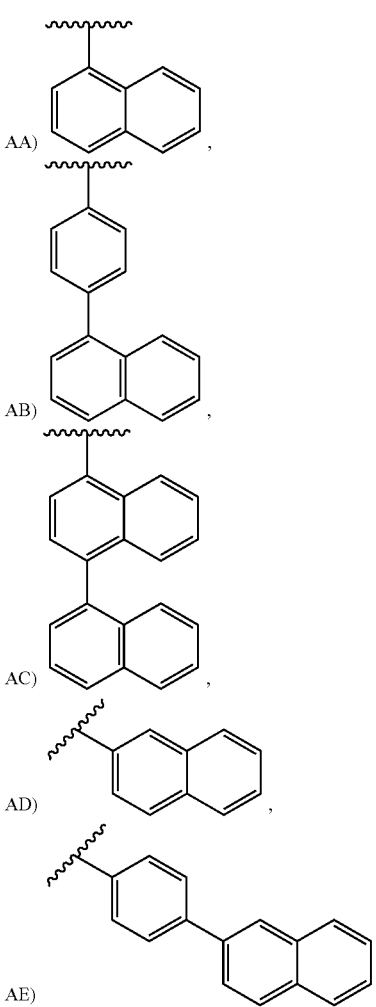

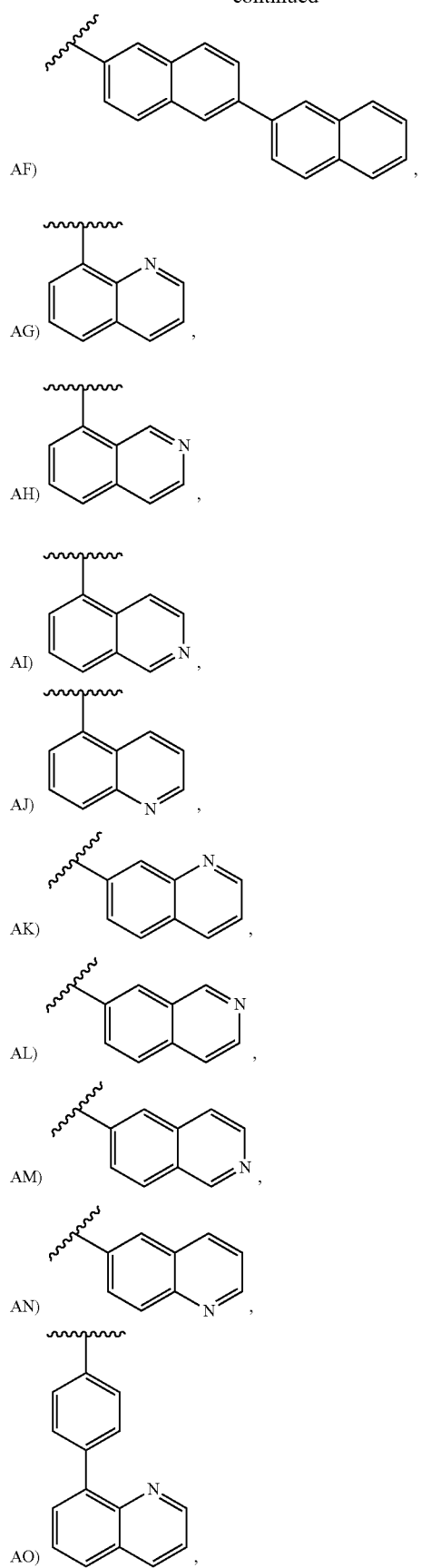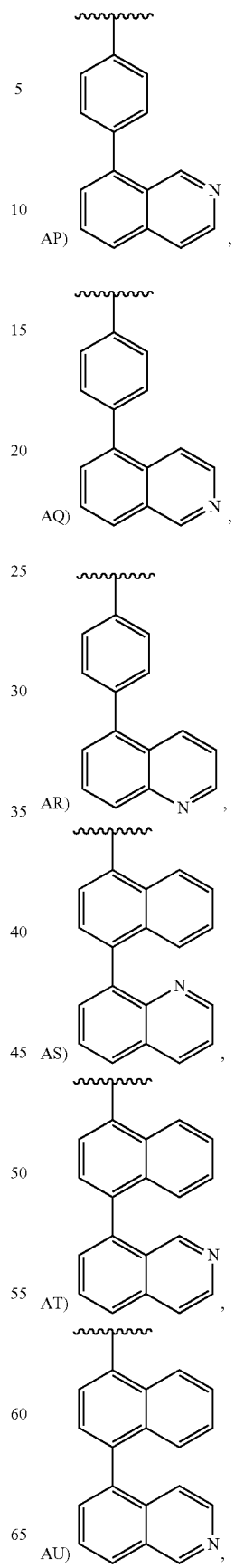

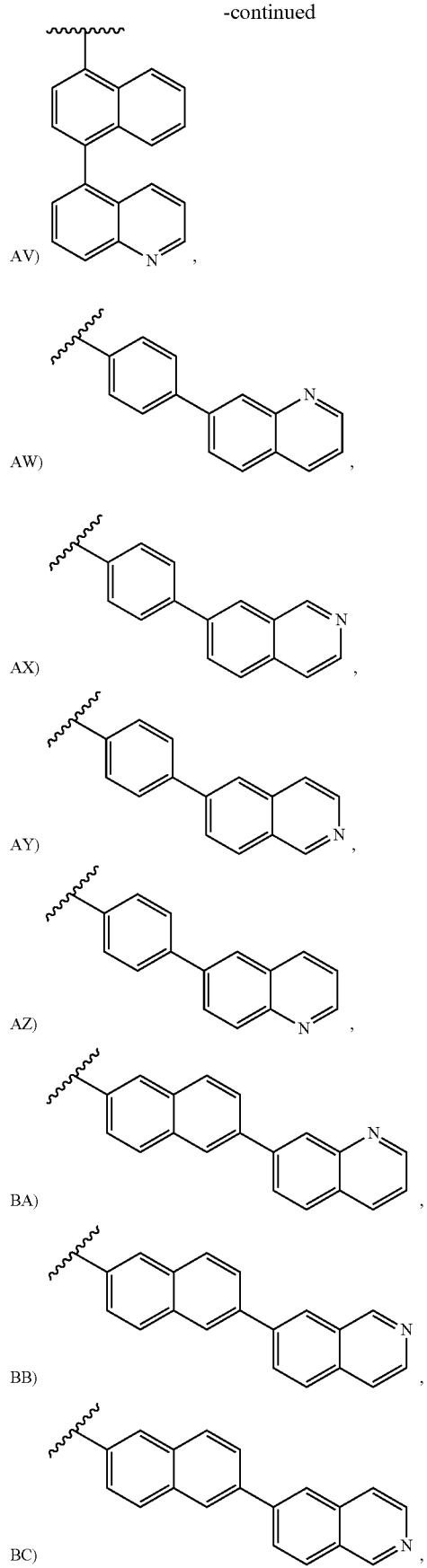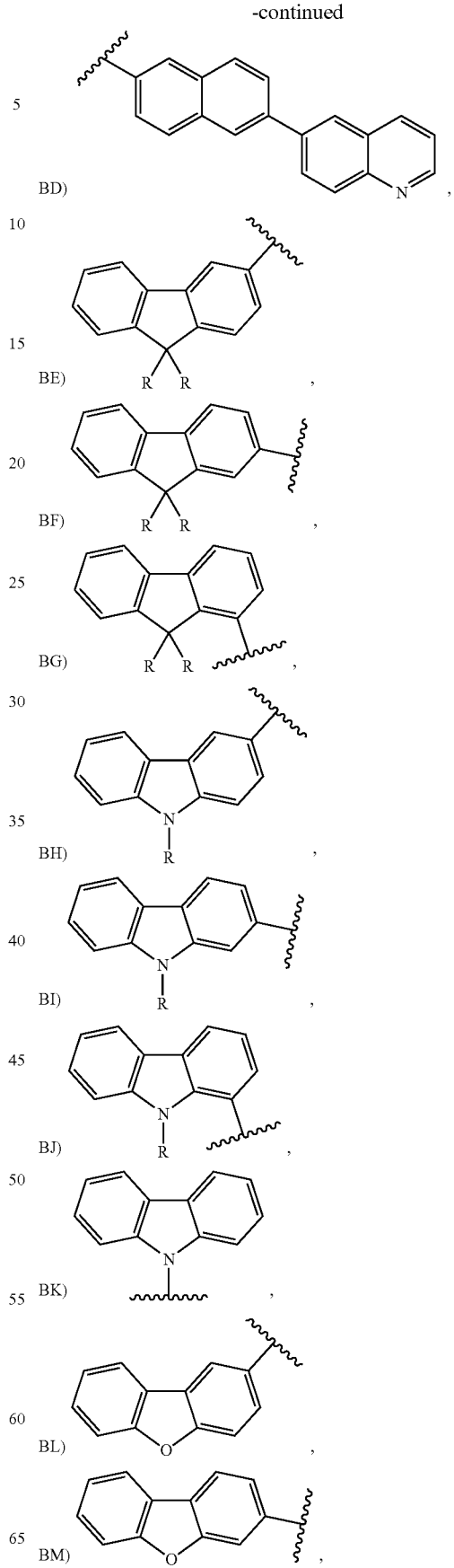

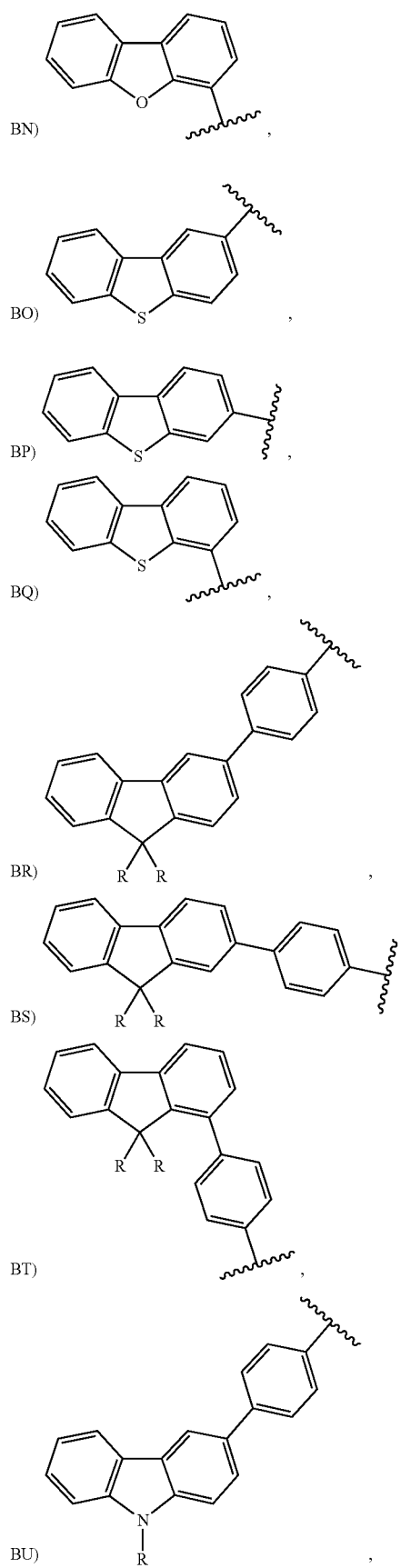
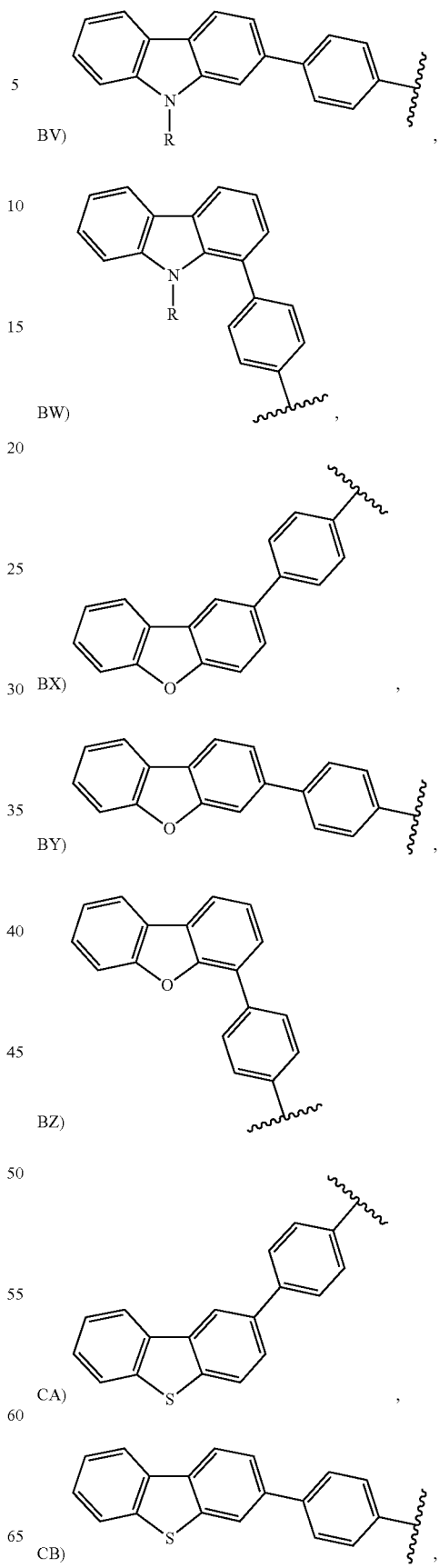

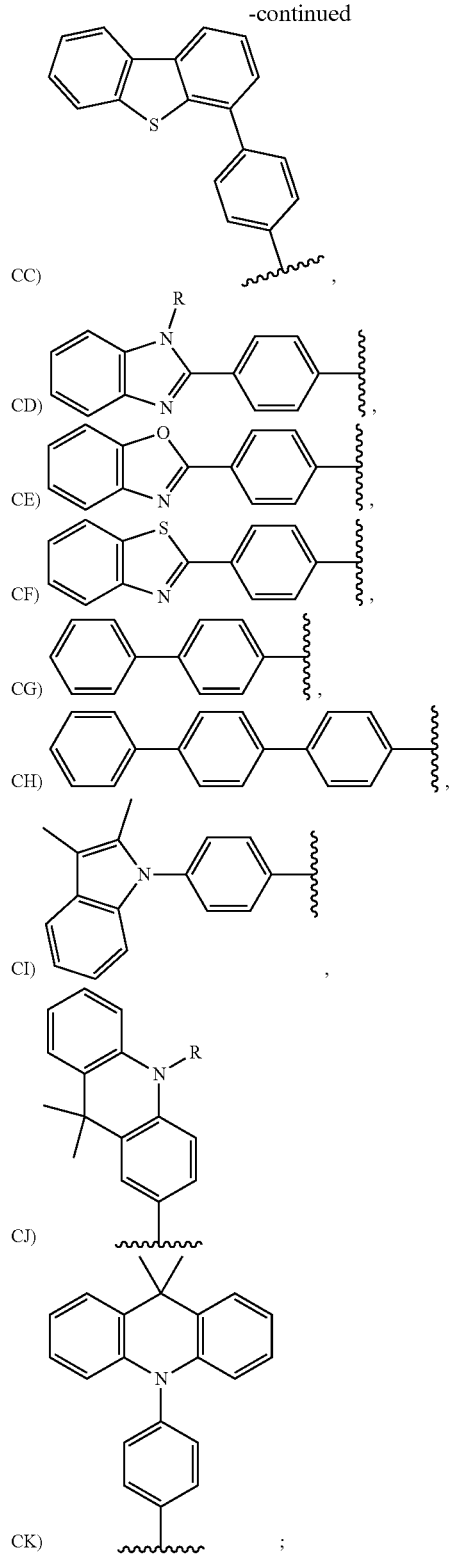

and wherein, for structures BE), BF), BG), BH), BI), BJ), BR), BS), BT), BU), BV), BW), CD), and CJ), each R is independently a $C_1$-$C_{20}$ alkyl, a substituted $C_1$-$C_{20}$ alkyl, a $C_6$-$C_{30}$ aryl, or a substituted $C_6$-$C_{30}$ aryl.

Some specific structures are labeled as follows:
DA)=GH) in which R is phenyl,
DB)=BI) in which R is a phenyl group,
DC)=BF) in which both R groups are methyl,
DD)=BF) in which both R groups are phenyl,
DE)=BR) in which both R groups are methyl,
DF)=BE) in which both R groups are methyl,
DG)=BE) in which both R groups are phenyl,
DH)=CJ) in which R is phenyl.

Preferably one or both of $R^1$ and $R^2$ are groups that are do not contain any heteroaryl group; more preferably both of $R^1$ and $R^2$ are groups that are do not contain any heteroaryl group.

More preferred $R^1$ and $R^2$ are each independently selected from the following groups: AB), AC), DA), DB), DC), DD), DE, BL), DF), DG), CE), AA), AE), AH), DH), and CK).

More preferred $R^1$ and $R^2$ are each independently selected from AE) and DC); more preferably $R^1$ is DC) and $R^2$ is AE).

Preferably, compound (I) has LUMO of −1.5 eV or lower; more preferably −1.6 eV or lower; more preferably −1.7 eV or lower. Preferably, compound (I) has LUMO of −2.2 eV or higher; more preferably −1.9 eV or higher.

Preferably, compound (I) has molecular weight of 500 or more. Preferably, compound (I) has molecular weight of 1000 or less; more preferably 900 or less; more preferably 800 or less; more preferably 700 or less; more preferably 600 or less.

Preferably, compound (I) has triplet energy of 2.1 eV or more; more preferably 2.15 eV or more; more preferably 2.2 eV or more. Preferably, compound (I) has 2.6 eV or less; more preferably 2.5 eV or less; more preferably 2.4 eV or less; more preferably 2.3 eV or less.

Preferably, compound (I) has HOMO of −4.8 eV or lower; more preferably −5.0 or lower; more preferably −5.2 eV or lower. Preferably, compound (I) has HOMO of −5.6 eV or higher; more preferably −5.5 eV or higher; more preferably −5.4 eV or higher.

Preferably, compound (I) has Tg of 90° C. or higher; more preferably 110° C. or higher; more preferably 130° C. or higher. Preferable, compound (I) has Tg or 200° C. or lower.

The composition of the present invention may be used for any purpose. A preferred use for the composition of the present invention is in one or more layers of an organic light-emitting diode (OLED). An OLED contains an anode, an emitting layer, and a cathode.

Preferably, an OLED contains the following layers in contact with each other in order as follows: a substrate, a conductive layer, a first hole injection layer, optionally a second hole injection layer, a hole transport layer, an emitting layer, an electron transport layer, and an electron injection layer. Preferably, when it is desired to operate the OLED, the electron injection layer is in contact with a metal cathode.

A preferred embodiment of an OLED is shown in FIG. 1. Glass substrate 1 is coated with a conductive layer. The remaining layers shown are a first hole injection layer 3, a second hole injection layer 4, a hole transport layer 5, an emitting layer 6, an electron transport layer 7, an electron injection layer 8, and a metal cathode 9. When it is desired to make the OLED emit light, the OLED is connected to a voltage source 10 via wires 11. The voltage is preferably applied so that the cathode is at a negative voltage relative to the anode.

A preferred substrate material is glass. A preferred conductive layer is indium tin oxide (ITO). The first hole injection layer preferably comprises one or more aromatic amines, more preferably one or more aromatic amines having two or more amine nitrogens. The second hole injection layer, if present, preferably comprises one or more nitrile, more preferably a nitrile having two or more nitrile groups. Preferably the emitting layer comprises one or more host and one or more dopant. Preferred hosts are aromatic amines. Preferred dopants are fluorescent dopants. Preferred dopants are aromatic amines having one or more fluorine atoms. Preferred electron injection layers comprise one or more organometal compounds; more preferably one or more metal quinolates; more preferably lithium quinolate.

A preferred use for the composition of the present invention is incorporation into the electron transport layer of an OLED. Preferably, the electron transport layer consists of the composition of the present invention.

Also contemplated are embodiments in which is used as a component of a hole transport layer. In such embodiments it is contemplated that the hole transport layer would also contain one or more dopants that would be chosen to have properties that appropriately match those of the host in order to create a layer that functioned properly as a hole transport layer.

The following are examples of the present invention.

Each operation in the following examples was performed at room temperature unless otherwise stated. Room temperature was approximately 23° C.

Glass transition temperature was measured using a DSC Q2000 instrument (TA Instruments) at a scan rate of 10° C./min, and in a nitrogen atmosphere for all cycles. The sample (about 7-10 mg) was scanned from room temperature to 300° C., cooled to −60° C., and reheated to 300° C. The glass transition temperature ($T_g$) was measured on the second heating scan. Data analysis was performed using TA Universal Analysis software (TA instruments). The $T_g$ was calculated using the "mid-point of inflection" methodology.

$^1$H-NMR-spectra (500 MHz or 400 MHz) were obtained on a Varian VNMRS-500 or a VNMRS-400 spectrometer, at 30° C., unless otherwise noted. The chemical shifts are referenced to TMS ($\delta$=0.00) in $CDCl_3$.

PREPARATIVE EXAMPLE 1: PREPARATION OF 4-BROMO-1,2,3,6,7,8-HEXAHYDROPYRENE (COMPOUND PE1)

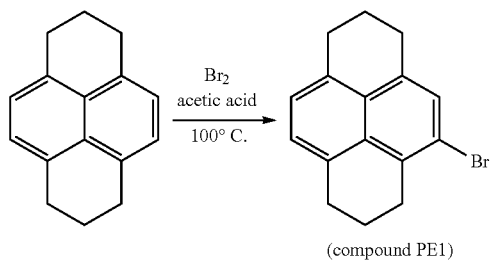

(compound PE1)

To a suspension of 1,2,3,6,7,8-hexahydropyrene (6.06 g, 29.1 mmol) in acetic acid (75 mL) a solution of bromine (1.57 mL, 30 mmol) in acetic acid (75 mL) was added dropwise within 1 h. The mixture was kept at room temperature (approximately 23° C.) for 30 min, then heated to 100° C. (the precipitate dissolves), then cooled to room temperature and diluted with water (75 mL). The solid was filtered off and dried. The crude product was purified by a reverse phase column chromatography using acetonitrile as an eluent. After purification, 2.01 g of powder was obtained (24.3% yield).

PREPARATIVE EXAMPLE 2: PREPARATION OF 4-BROMO-PYRENE (COMPOUND PE2)

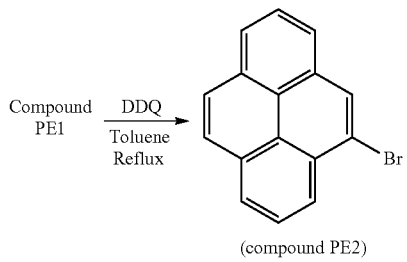

(compound PE2)

To a solution 4-bromo-1,2,3,6,7,8-hexahydropyrene (2.01 g, 7.0 mmol) in toluene (135 mL), 2,3-Dichloro-5,6-dicyano-1,4-benzoquinone (DDQ) (5.30 g, 23 mmol) was added in one portion, the flask was flushed with argon and the mixture was refluxed for 20 min, then cooled to room temperature and filtered. The solution was washed with 10% NaOH (30 mL), water (50 mL), and dried over sodium sulfate. After silica column separation using methylene chloride as an eluent, pure product (1.0 g) was obtained (51.0% yield).

PREPARATIVE EXAMPLE 3: PREPARATION OF 9,9-DIMETHYL-N-(PYREN-4-YL)-9H-FLUORENE-2-CARBOXAMIDE (COMPOUND PE3)

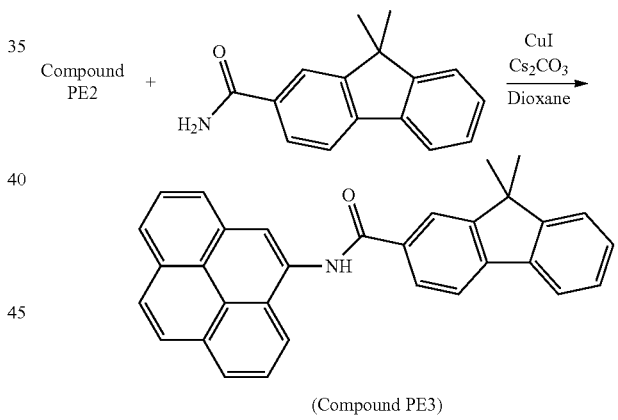

(Compound PE3)

4-bromopyrene (1.00 g, 3.56 mmol), 9,9-dimethyl-9H-fluorene-2-carboxamide (1.27 g, 5.34 mmol), N,N-dimethylethylenediamine (DMEDA) (0.13 g, 1.42 mmol), $Cs_2CO_3$ (2.55 g, 7.83 mmol) dioxane (100 mL) were mixed in a 250 mL round flask, and the mixture was bubbled with Nitrogen for 30 minutes. After purging $N_2$, CuI (0.14 g, 0.71 mmol) was added to the mixture. The reaction mixture was stirred for 15 h at 120° C. under nitrogen. After check the conversion of the reaction by LC/MS, additional CuI (0.14 g) and DMEDA (0.13 g) were added to the mixture, if necessary and the mixture was heated at 120° C. overnight. The solution was then cooled to room temperature and the product was precipitated under ice water. The crude product was purified by column chromatography on silica gel chromatography with the mixture of methanol and methylene chloride (0:10 to 0.5:9.5). After purification, 1.27 g of powder was obtained (81.4% yield).

WORKING EXAMPLE 1: SYNTHESIS OF INVENTIVE COMPOUND EXAMPLE 1 (EX1)

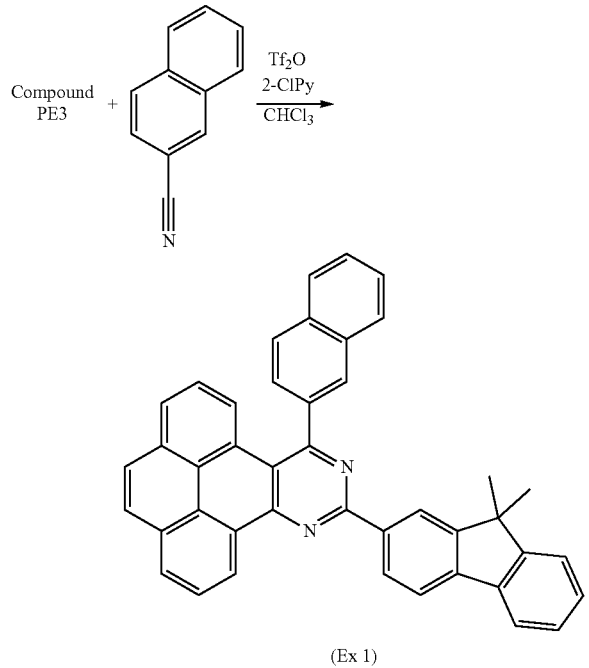

(Ex 1)

Trifluoromethanesulfonic anhydride (0.58 mL, 3.48 mmol) was added via syringe over 1 min to a stirred mixture of 9,9-dimethyl-N-(pyren-4-yl)-9H-fluorene-2-carboxamide (1.27 g, 2.90 mmol), 2-chloropyridine (2-ClPy) (0.33 mL, 3.48 mmol), and 2-naphthonitrile (0.53 g, 3.48 mmol) in chloroform (50 mL) at −78° C. After 5 min, the reaction mixture was placed in an ice-water bath for 5 minutes and warmed to 0° C. The resulting solution was allowed to warm to room temperature for 5 minutes before the reaction vessel was placed into a preheated oil bath at 45° C. and maintained at that temperature. After 16 h, the reaction mixture was allowed to cool to room temperature, and aqueous sodium hydroxide solution (1 mL, 1N) was introduced at to neutralize the trifluoromethanesulfonate salts. Chloroform (5 mL) was added to dilute the mixture, and the layers were separated. The organic layer was washed with water (2 mL) and was filtered through a phase separate filter paper for removing water content. The volatiles were removed under reduced pressure and the residue was purified by flash column chromatography with Hexane and methylene chloride mixture (7:3). After column separation, pure product (0.80 g, 99.6% yield) was obtained. After sublimation, 0.27 g of pure compound (Ex1) was obtained. 1H NMR (400 MHz, Chloroform-d) δ 9.79 (dd, J=7.8, 1.2 Hz, 1H), 8.91 (dt, J=4.1, 2.0 Hz, 2H), 8.48-8.42 (m, 1H), 8.40-8.33 (m, 1H), 8.18 (t, J=7.7 Hz, 1H), 8.10-7.89 (m, 8H), 7.86-7.78 (m, 1H), 7.70 (dd, J=8.4, 1.7 Hz, 1H), 7.59 (tt, J=7.1, 5.4 Hz, 2H), 7.55-7.44 (m, 2H), 7.43-7.32 (m, 2H), 1.65 (s, 6H).

EXAMPLE 2

The HOMO and LUMO values were determined as described above for various embodiments of compound (I). Results were as follows. All values are in eV.

TABLE 1

Results of Calculations

| R1 | R2 | HOMO − 1 | HOMO | LUMO | LUMO + 1 | ΔLUMO | T1 | λ− |
|----|----|----------|------|------|----------|-------|-----|-----|
| CE | CE | −5.9557 | −5.6088 | −2.1825 | −1.9202 | 0.2623 | 2.1968 | 0.2969 |
| AE | CE | −5.8004 | −5.5272 | −2.0685 | −1.7790 | 0.2895 | 2.1977 | 0.3976 |
| CE | AB | −5.7631 | −5.5552 | −2.0666 | −1.7872 | 0.2795 | 2.2404 | 0.2495 |
| AB | CE | −5.6961 | −5.5057 | −2.0511 | −1.7953 | 0.2558 | 2.2194 | 0.4020 |
| AC | CE | −5.7310 | −5.4706 | −2.0506 | −1.8029 | 0.2476 | 2.2378 | 0.3958 |
| CE | BL | −5.9261 | −5.5585 | −2.0506 | −1.7540 | 0.2966 | 2.2429 | 0.2726 |
| CE | AE | −5.9187 | −5.5585 | −2.0478 | −1.7986 | 0.2492 | 2.2683 | 0.2457 |
| CE | DE | −5.6858 | −5.5008 | −2.0443 | −1.7722 | 0.2721 | 2.2317 | 0.2420 |
| AA | CE | −5.7944 | −5.4923 | −2.0432 | −1.7956 | 0.2476 | 2.2454 | 0.4218 |
| DE | CE | −5.6744 | −5.4208 | −2.0372 | −1.7918 | 0.2454 | 2.2093 | 0.3677 |
| CE | AC | −5.7832 | −5.5500 | −2.0372 | −1.7608 | 0.2765 | 2.2778 | 0.2747 |
| CE | DC | −5.8730 | −5.4970 | −2.0350 | −1.7553 | 0.2797 | 2.2215 | 0.2474 |
| CE | DD | −5.8733 | −5.4951 | −2.0345 | −1.7599 | 0.2746 | 2.2297 | 0.2431 |
| CE | DG | −5.8896 | −5.5438 | −2.0329 | −1.7447 | 0.2882 | 2.2506 | 0.2656 |
| BL | CE | −5.9753 | −5.5500 | −2.0320 | −1.7768 | 0.2552 | 2.2310 | 0.4789 |
| DG | CE | −5.7685 | −5.5359 | −2.0310 | −1.7752 | 0.2558 | 2.2256 | 0.4356 |
| DD | CE | −5.8085 | −5.4676 | −2.0304 | −1.7736 | 0.2569 | 2.2041 | 0.3797 |
| DC | CE | −5.8017 | −5.4548 | −2.0195 | −1.7738 | 0.2457 | 2.2020 | 0.4060 |
| CE | AA | −5.9029 | −5.5732 | −2.0195 | −1.7580 | 0.2615 | 2.3078 | 0.2694 |
| CE | DF | −5.8714 | −5.5138 | −2.0176 | −1.7257 | 0.2920 | 2.2507 | 0.2671 |
| CK | CK | −4.9405 | −4.8175 | −2.0174 | −1.8906 | 0.1268 | 2.2875 | 0.3491 |
| DF | CE | −5.7446 | −5.5250 | −2.0065 | −1.7529 | 0.2536 | 2.2290 | 0.4564 |
| DB | CE | −5.4330 | −5.3517 | −2.0008 | −1.7341 | 0.2667 | 2.1978 | 0.4153 |
| CE | DB | −5.5408 | −5.4328 | −2.0008 | −1.7063 | 0.2944 | 2.2239 | 0.2644 |
| AH | CE | −5.9639 | −5.4790 | −1.9507 | −1.6955 | 0.2552 | 2.2685 | 0.3668 |
| CE | DA | −5.5810 | −5.3772 | −1.9485 | −1.6476 | 0.3009 | 2.2417 | 0.2728 |
| CE | AH | −5.8534 | −5.5087 | −1.9267 | −1.6699 | 0.2569 | 2.3847 | 0.2846 |
| DA | CE | −5.6009 | −5.2507 | −1.9221 | −1.6693 | 0.2528 | 2.2055 | 0.4999 |
| AE | AB | −5.7236 | −5.4679 | −1.8614 | −1.6963 | 0.1652 | 2.2583 | 0.3057 |
| DF | CK | −5.5634 | −4.8954 | −1.8598 | −1.7703 | 0.0895 | 2.2934 | 0.3971 |
| DF | CK | −5.5582 | −5.0306 | −1.8595 | −1.7654 | 0.0942 | 2.2929 | 0.3939 |
| AE | DE | −5.6464 | −5.4303 | −1.8584 | −1.6827 | 0.1758 | 2.2457 | 0.3169 |
| AE | AE | −5.7549 | −5.4757 | −1.8525 | −1.7072 | 0.1453 | 2.3011 | 0.2767 |

TABLE 1-continued

Results of Calculations

| R1 | R2 | HOMO − 1 | HOMO | LUMO | LUMO + 1 | ΔLUMO | T1 | λ− |
|---|---|---|---|---|---|---|---|---|
| AE | DD | −5.7258 | −5.4191 | −1.8503 | −1.6699 | 0.1804 | 2.2466 | 0.3021 |
| AB | AB | −5.6477 | −5.4657 | −1.8454 | −1.7153 | 0.1301 | 0.0000 | 0.3046 |
| AC | AB | −5.6303 | −5.3906 | −1.8435 | −1.7126 | 0.1309 | 2.1655 | 0.2942 |
| AE | DC | −5.7340 | −5.4202 | −1.8427 | −1.6683 | 0.1744 | 2.2374 | 0.2902 |
| DE | DE | −5.5631 | −5.3674 | −1.8418 | −1.6865 | 0.1554 | 2.2540 | 0.2781 |
| AA | AB | −5.6989 | −5.4431 | −1.8383 | −1.7121 | 0.1263 | 2.2744 | 0.3208 |
| AC | DE | −5.5963 | −5.3968 | −1.8380 | −1.7031 | 0.1350 | 2.2641 | 0.2985 |
| DD | DE | −5.6191 | −5.3879 | −1.8367 | −1.6699 | 0.1668 | 2.2532 | 0.2888 |
| DE | AB | −5.6170 | −5.3811 | −1.8367 | −1.6897 | 0.1469 | 2.2709 | 0.2609 |
| AE | BL | −5.7628 | −5.4768 | −1.8367 | −1.6819 | 0.1548 | 2.2659 | 0.2602 |
| AB | DE | −5.5974 | −5.4262 | −1.8331 | −1.6952 | 0.1380 | 2.2702 | 0.3148 |
| DC | AE | −5.7332 | −5.3838 | −1.8331 | −1.6647 | 0.1684 | 2.2121 | 0.2909 |
| AA | DE | −5.6113 | −5.4123 | −1.8331 | −1.6995 | 0.1336 | 2.2905 | 0.3364 |
| DD | AB | −5.6970 | −5.4148 | −1.8323 | −1.6742 | 0.1581 | 2.2644 | 0.2696 |
| AB | AE | −5.6627 | −5.4616 | −1.8318 | −1.7243 | 0.1075 | 2.2976 | 0.2569 |
| AA | DD | −5.6869 | −5.3952 | −1.8299 | −1.6889 | 0.1410 | 2.2639 | 0.3125 |
| AC | AE | −5.7038 | −5.4200 | −1.8280 | −1.7292 | 0.0988 | 2.2876 | 0.2694 |
| DE | AE | −5.6371 | −5.3832 | −1.8280 | −1.7069 | 0.1211 | 2.2945 | 0.2354 |
| DC | AB | −5.7000 | −5.4083 | −1.8255 | −1.6827 | 0.1429 | 2.2641 | 0.2995 |
| AB | DD | −5.6235 | −5.4257 | −1.8253 | −1.6873 | 0.1380 | 2.4218 | 0.2986 |
| DD | DD | −5.7223 | −5.3783 | −1.8253 | −1.6601 | 0.1652 | 2.2499 | 0.2751 |
| AC | DC | −5.6616 | −5.3884 | −1.8233 | −1.6881 | 0.1352 | 2.2601 | 0.2741 |
| DD | DC | −5.7258 | −5.3838 | −1.8231 | −1.6557 | 0.1673 | 2.2463 | 0.2615 |
| DC | DE | −5.6088 | −5.3702 | −1.8220 | −1.6674 | 0.1546 | 2.2529 | 0.3005 |
| DD | AE | −5.7715 | −5.4181 | −1.8217 | −1.6927 | 0.1290 | 2.2914 | 0.2367 |
| DE | BL | −5.6322 | −5.3860 | −1.8212 | −1.6636 | 0.1576 | 2.2705 | 0.2491 |
| AC | BL | −5.7013 | −5.4254 | −1.8206 | −1.6821 | 0.1385 | 2.2661 | 0.3065 |
| AC | DD | −5.6657 | −5.3879 | −1.8204 | −1.6862 | 0.1342 | 2.2632 | 0.2986 |
| DE | DC | −5.5870 | −5.3541 | −1.8198 | −1.6661 | 0.1537 | 2.2526 | 0.2468 |
| DE | DD | −5.5862 | −5.3541 | −1.8193 | −1.6691 | 0.1502 | 2.2592 | 0.2666 |
| AE | AC | −5.7261 | −5.4777 | −1.8176 | −1.6897 | 0.1279 | 2.2804 | 0.3710 |
| AE | DG | −5.7470 | −5.4619 | −1.8168 | −1.6663 | 0.1505 | 2.2750 | 0.2986 |
| AB | DC | −5.6251 | −5.4197 | −1.8165 | −1.6816 | 0.1350 | 2.2613 | 0.2801 |
| DG | AB | −5.7225 | −5.4850 | −1.8149 | −1.7050 | 0.1099 | 2.2851 | 0.3422 |
| DD | BL | −5.7732 | −5.4205 | −1.8138 | −1.6492 | 0.1646 | 0.0000 | 0.2452 |
| AC | DG | −5.6763 | −5.4047 | −1.8125 | −1.6813 | 0.1312 | 2.2803 | 0.2832 |
| DC | DD | −5.7084 | −5.3628 | −1.8125 | −1.6598 | 0.1527 | 2.2505 | 0.2987 |
| AA | AE | −5.7511 | −5.4374 | −1.8125 | −1.7227 | 0.0898 | 2.2902 | 0.2937 |
| DG | DE | −5.6529 | −5.4439 | −1.8100 | −1.6900 | 0.1200 | 2.2745 | 0.3610 |
| AB | BL | −5.6575 | −5.4616 | −1.8062 | −1.6870 | 0.1192 | 2.2834 | 0.2559 |
| DE | DG | −5.6216 | −5.3737 | −1.8043 | −1.6574 | 0.1469 | 2.2796 | 0.2577 |
| AA | BL | −5.7538 | −5.4442 | −1.8043 | −1.6748 | 0.1295 | 2.2715 | 0.2804 |
| AC | AC | −5.6597 | −5.4279 | −1.8038 | −1.6889 | 0.1148 | 2.2874 | 0.3362 |
| DG | DD | −5.6932 | −5.4287 | −1.8029 | −1.6748 | 0.1282 | 2.2835 | 0.3137 |
| AB | DG | −5.6450 | −5.4502 | −1.8019 | −1.6791 | 0.1227 | 2.2841 | 0.2819 |
| DC | DC | −5.7100 | −5.3606 | −1.8016 | −1.6525 | 0.1491 | 2.2475 | 0.2704 |
| AE | DF | −5.7378 | −5.4507 | −1.8010 | −1.6511 | 0.1499 | 2.2802 | 0.2665 |
| DE | AC | −5.6107 | −5.3898 | −1.7994 | −1.6729 | 0.1265 | 2.2974 | 0.2848 |
| DG | AE | −5.7302 | −5.4858 | −1.7983 | −1.7118 | 0.0865 | 2.3005 | 0.3066 |
| AE | DB | −5.4861 | −5.3734 | −1.7975 | −1.6361 | 0.1614 | 2.2579 | 0.2966 |
| DD | DG | −5.7604 | −5.4045 | −1.7970 | −1.6429 | 0.1540 | 2.2741 | 0.2662 |
| AC | AA | −5.6706 | −5.4202 | −1.7959 | −1.6800 | 0.1159 | 2.2883 | 0.3165 |
| DB | DE | −5.3568 | −5.3122 | −1.7959 | −1.6421 | 0.1537 | 2.2525 | 0.3316 |
| DD | AC | −5.7073 | −5.4240 | −1.7950 | −1.6576 | 0.1374 | 2.2945 | 0.3233 |
| DE | AA | −5.6145 | −5.3846 | −1.7923 | −1.6604 | 0.1320 | 2.2951 | 0.2638 |
| AA | AC | −5.6877 | −5.4439 | −1.7921 | −1.6868 | 0.1053 | 2.2922 | 0.3875 |
| BL | DE | −5.6668 | −5.4461 | −1.7915 | −1.6955 | 0.0961 | 2.2864 | 0.4012 |
| DC | BL | −5.7617 | −5.4026 | −1.7904 | −1.6560 | 0.1344 | 2.2764 | 0.2386 |
| BL | AB | −5.7538 | −5.4994 | −1.7891 | −1.7186 | 0.0705 | 2.2895 | 0.4187 |
| AE | AA | −5.7527 | −5.4921 | −1.7888 | −1.6824 | 0.1064 | 2.3262 | 0.2676 |
| DB | AB | −5.3813 | −5.3174 | −1.7872 | −1.6495 | 0.1377 | 2.2666 | 0.3093 |
| DG | DC | −5.7176 | −5.4311 | −1.7872 | −1.6740 | 0.1132 | 2.2792 | 0.3124 |
| DE | DF | −5.5968 | −5.3593 | −1.7866 | −1.6370 | 0.1497 | 2.2765 | 0.2488 |
| AA | AA | −5.7119 | −5.4374 | −1.7861 | −1.6740 | 0.1121 | 2.2887 | 0.3018 |
| AC | DF | −5.6839 | −5.3982 | −1.7839 | −1.6552 | 0.1287 | 2.2764 | 0.3057 |
| AA | DC | −5.7043 | −5.4107 | −1.7833 | −1.6865 | 0.0969 | 2.2785 | 0.3679 |
| AB | DF | −5.6319 | −5.4281 | −1.7825 | −1.6555 | 0.1271 | 2.2806 | 0.2644 |
| DF | DE | −5.6404 | −5.4295 | −1.7814 | −1.6710 | 0.1105 | 2.2858 | 0.3847 |
| BL | AE | −5.8989 | −5.4978 | −1.7812 | −1.7175 | 0.0637 | 2.3016 | 0.3906 |
| DC | DG | −5.7525 | −5.3900 | −1.7804 | −1.6438 | 0.1366 | 2.2728 | 0.2788 |
| DB | AE | −5.3811 | −5.3138 | −1.7787 | −1.6644 | 0.1143 | 2.2961 | 0.2800 |
| DD | DB | −5.4714 | −5.3343 | −1.7782 | −1.6201 | 0.1581 | 2.2615 | 0.2482 |
| AB | AC | −5.6352 | −5.4763 | −1.7779 | −1.6971 | 0.0808 | 2.3201 | 0.3431 |
| DB | DC | −5.3525 | −5.3032 | −1.7779 | −1.6296 | 0.1483 | 2.2501 | 0.2982 |
| DE | DB | −5.4627 | −5.3291 | −1.7776 | −1.6334 | 0.1442 | 2.2686 | 0.2488 |
| DD | DF | −5.7525 | −5.3952 | −1.7774 | −1.6214 | 0.1559 | 2.2776 | 0.2486 |

TABLE 1-continued

Results of Calculations

| R1 | R2 | HOMO − 1 | HOMO | LUMO | LUMO + 1 | ΔLUMO | T1 | λ− |
|---|---|---|---|---|---|---|---|---|
| DF | AB | −5.6961 | −5.4613 | −1.7771 | −1.6821 | 0.0950 | 2.2890 | 0.3651 |
| DC | AA | −5.7247 | −5.4034 | −1.7746 | −1.6511 | 0.1235 | 2.2944 | 0.2788 |
| DD | AA | −5.7680 | −5.4260 | −1.7738 | −1.6538 | 0.1200 | 2.3149 | 0.2302 |
| BL | DD | −5.8961 | −5.4523 | −1.7719 | −1.6881 | 0.0838 | 2.2899 | 0.3773 |
| AB | AA | −5.6643 | −5.4681 | −1.7714 | −1.6854 | 0.0860 | 2.3209 | 0.2558 |
| AE | AH | −5.6730 | −5.3821 | −1.7708 | −1.5929 | 0.1780 | 2.3438 | 0.3365 |
| AC | DB | −5.4730 | −5.3560 | −1.7695 | −1.6541 | 0.1154 | 2.2732 | 0.2929 |
| DC | AC | −5.7280 | −5.4191 | −1.7678 | −1.6680 | 0.0999 | 2.3268 | 0.3152 |
| DG | BL | −5.7386 | −5.4834 | −1.7651 | −1.6789 | 0.0862 | 2.2895 | 0.2626 |
| AB | DB | −5.4806 | −5.3729 | −1.7643 | −1.6476 | 0.1167 | 2.2795 | 0.2850 |
| DF | AE | −5.7043 | −5.4730 | −1.7643 | −1.6908 | 0.0735 | 2.3042 | 0.3514 |
| DF | AE | −5.7043 | −5.4730 | −1.7643 | −1.6908 | 0.0735 | 2.3042 | 0.3514 |
| BL | DC | −5.8774 | −5.4409 | −1.7638 | −1.6838 | 0.0800 | 2.2828 | 0.3880 |
| AA | DG | −5.7402 | −5.4436 | −1.7635 | −1.6756 | 0.0879 | 2.2898 | 0.3653 |
| DB | BL | −5.3868 | −5.3231 | −1.7632 | −1.6304 | 0.1328 | 2.2742 | 0.2655 |
| DC | DF | −5.7438 | −5.3797 | −1.7632 | −1.6239 | 0.1393 | 2.2770 | 0.2537 |
| DB | DD | −5.3310 | −5.3005 | −1.7613 | −1.6084 | 0.1529 | 2.2535 | 0.3248 |
| DF | DC | −5.6874 | −5.4314 | −1.7608 | −1.6582 | 0.1026 | 2.2830 | 0.3551 |
| DG | DG | −5.7258 | −5.4728 | −1.7597 | −1.6702 | 0.0895 | 2.2889 | 0.3209 |
| DE | AH | −5.5617 | −5.3054 | −1.7586 | −1.6076 | 0.1510 | 2.3207 | 0.2595 |
| DB | DG | −5.3726 | −5.3054 | −1.7580 | −1.6293 | 0.1287 | 2.2755 | 0.2946 |
| AH | AB | −5.6864 | −5.4148 | −1.7570 | −1.5605 | 0.1965 | 2.5023 | 0.2622 |
| DC | DB | −5.4613 | −5.3187 | −1.7526 | −1.6171 | 0.1355 | 2.2644 | 0.2731 |
| DD | AH | −5.6932 | −5.3247 | −1.7510 | −1.5948 | 0.1562 | 2.3187 | 0.2788 |
| AH | DE | −5.6061 | −5.3759 | −1.7510 | −1.5632 | 0.1878 | 2.2911 | 0.2686 |
| DF | DD | −5.6842 | −5.4045 | −1.7496 | −1.6353 | 0.1143 | 2.2853 | 0.3779 |
| AA | DB | −5.4733 | −5.3536 | −1.7496 | −1.6419 | 0.1078 | 2.2717 | 0.3165 |
| BL | BL | −5.9380 | −5.4994 | −1.7480 | −1.6857 | 0.0623 | 2.2841 | 0.3295 |
| DG | DB | −5.4839 | −5.3791 | −1.7474 | −1.6478 | 0.0996 | 2.2825 | 0.2667 |
| AA | DF | −5.7304 | −5.4328 | −1.7466 | −1.6527 | 0.0939 | 2.2888 | 0.3189 |
| DB | AC | −5.3851 | −5.3204 | −1.7442 | −1.6394 | 0.1048 | 2.2912 | 0.3759 |
| DG | AA | −5.7130 | −5.4872 | −1.7439 | −1.6702 | 0.0737 | 2.3031 | 0.3320 |
| AH | AE | −5.8069 | −5.4243 | −1.7420 | −1.5834 | 0.1586 | 2.3095 | 0.2561 |
| DG | AH | −5.6668 | −5.3952 | −1.7414 | −1.5858 | 0.1556 | 2.3263 | 0.3742 |
| BL | DG | −5.8629 | −5.4853 | −1.7406 | −1.6887 | 0.0520 | 2.2903 | 0.3907 |
| DF | BL | −5.7108 | −5.4747 | −1.7401 | −1.6560 | 0.0841 | 2.2843 | 0.2981 |
| DG | AC | −5.7304 | −5.5079 | −1.7385 | −1.6865 | 0.0520 | 2.3235 | 0.3958 |
| DG | DF | −5.7171 | −5.4630 | −1.7368 | −1.6481 | 0.0887 | 2.2888 | 0.2883 |
| AH | DC | −5.7805 | −5.3626 | −1.7346 | −1.5406 | 0.1940 | 2.5008 | 0.2570 |
| DB | AA | −5.3860 | −5.3149 | −1.7330 | −1.6263 | 0.1067 | 2.2985 | 0.3027 |
| DC | AH | −5.6806 | −5.3098 | −1.7327 | −1.5866 | 0.1461 | 2.3191 | 0.3131 |
| AH | DD | −5.7865 | −5.3974 | −1.7327 | −1.5333 | 0.1995 | 2.2897 | 0.2791 |
| AH | BL | −5.9361 | −5.4406 | −1.7311 | −1.5298 | 0.2014 | 2.2914 | 0.3141 |
| DF | AC | −5.6937 | −5.4687 | −1.7303 | −1.6688 | 0.0615 | 2.3035 | 0.4458 |
| AE | DA | −5.5664 | −5.2929 | −1.7303 | −1.5684 | 0.1619 | 2.2491 | 0.2557 |
| DB | DF | −5.3612 | −5.3027 | −1.7276 | −1.6016 | 0.1260 | 2.2826 | 0.2753 |
| DB | DB | −5.3231 | −5.2992 | −1.7268 | −1.5964 | 0.1303 | 2.2702 | 0.2920 |
| DF | DG | −5.7002 | −5.4602 | −1.7235 | −1.6519 | 0.0716 | 2.2923 | 0.3621 |
| BL | AC | −5.7813 | −5.5174 | −1.7216 | −1.7023 | 0.0193 | 2.3211 | 0.5358 |
| DE | DA | −5.4597 | −5.2643 | −1.7213 | −1.5504 | 0.1709 | 2.2505 | 0.2545 |
| BL | AA | −5.8798 | −5.4978 | −1.7213 | −1.6748 | 0.0465 | 2.3051 | 0.4160 |
| DH | CK | −4.8954 | −4.8608 | −1.7210 | −1.6565 | 0.0645 | 2.2181 | 0.4380 |
| AH | AC | −5.7424 | −5.4469 | −1.7180 | −1.5254 | 0.1927 | 2.5132 | 0.2846 |
| DD | DA | −5.5215 | −5.2635 | −1.7178 | −1.5385 | 0.1793 | 2.2480 | 0.2394 |
| AH | DG | −5.7732 | −5.4333 | −1.7151 | −1.5352 | 0.1799 | 2.4632 | 0.3016 |
| BL | DB | −5.5057 | −5.3873 | −1.7131 | −1.6514 | 0.0618 | 2.2821 | 0.4130 |
| DF | AA | −5.6883 | −5.4706 | −1.7129 | −1.6549 | 0.0580 | 2.3047 | 0.3724 |
| AH | DF | −5.7712 | −5.3957 | −1.7112 | −1.4914 | 0.2199 | 2.2944 | 0.2893 |
| AB | DA | −5.5220 | −5.3019 | −1.7093 | −1.5670 | 0.1423 | 2.2572 | 0.2663 |
| BL | DF | −5.8526 | −5.4730 | −1.7091 | −1.6593 | 0.0498 | 2.2918 | 0.3674 |
| AH | AA | −5.7644 | −5.4521 | −1.7061 | −1.5104 | 0.1956 | 2.3342 | 0.3117 |
| DF | DB | −5.4763 | −5.3642 | −1.7055 | −1.6231 | 0.0824 | 2.2807 | 0.3712 |
| DF | DF | −5.6915 | −5.4491 | −1.7036 | −1.6302 | 0.0735 | 2.2919 | 0.3217 |
| AC | DA | −5.5068 | −5.2913 | −1.7028 | −1.5749 | 0.1279 | 2.2625 | 0.3236 |
| AH | DB | −5.4276 | −5.3117 | −1.7020 | −1.5020 | 0.2000 | 2.2935 | 0.2705 |
| AA | DA | −5.4997 | −5.2929 | −1.7004 | −1.5594 | 0.1409 | 2.2558 | 0.2750 |
| DC | DA | −5.5027 | −5.2567 | −1.6976 | −1.5395 | 0.1581 | 2.2514 | 0.2455 |
| AC | AH | −5.6630 | −5.3560 | −1.6887 | −1.5964 | 0.0922 | 2.3155 | 0.3541 |
| AB | AH | −5.6053 | −5.4080 | −1.6859 | −1.6005 | 0.0854 | 2.3271 | 0.3378 |
| DA | DE | −5.4921 | −5.1993 | −1.6859 | −1.5972 | 0.0887 | 2.2797 | 0.4199 |
| AA | AH | −5.6825 | −5.3655 | −1.6794 | −1.5964 | 0.0830 | 2.3163 | 0.3627 |
| DA | AB | −5.5500 | −5.2145 | −1.6745 | −1.6130 | 0.0615 | 0.0000 | 0.4233 |
| DG | DA | −5.5753 | −5.3024 | −1.6742 | −1.5621 | 0.1121 | 2.2644 | 0.2640 |
| DA | DD | −5.4986 | −5.1704 | −1.6723 | −1.5806 | 0.0917 | 2.2811 | 0.3822 |
| DB | DA | −5.2782 | −5.2328 | −1.6614 | −1.5205 | 0.1410 | 2.2554 | 0.2599 |
| DA | AE | −5.5587 | −5.2042 | −1.6612 | −1.6122 | 0.0490 | 2.2970 | 0.5081 |

TABLE 1-continued

Results of Calculations

| R1 | R2 | HOMO − 1 | HOMO | LUMO | LUMO + 1 | ΔLUMO | T1 | λ− |
|----|----|----------|------|------|----------|-------|----|----|
| AH | DA | −5.5176 | −5.2309 | −1.6497 | −1.4027 | 0.2471 | 2.2729 | 0.3031 |
| BL | AH | −5.8529 | −5.4445 | −1.6489 | −1.6100 | 0.0389 | 2.3279 | 0.4671 |
| BL | DA | −5.5914 | −5.3122 | −1.6454 | −1.5711 | 0.0743 | 2.2699 | 0.3200 |
| DA | DC | −5.5043 | −5.1881 | −1.6440 | −1.5806 | 0.0634 | 2.2790 | 0.3995 |
| DA | AH | −5.4831 | −5.1264 | −1.6416 | −1.4761 | 0.1654 | 2.3213 | 0.4633 |
| DB | AH | −5.3223 | −5.2458 | −1.6408 | −1.5515 | 0.0893 | 2.3257 | 0.3648 |
| DF | DA | −5.5664 | −5.2877 | −1.6391 | −1.5428 | 0.0963 | 2.2686 | 0.2869 |
| DA | BL | −5.5585 | −5.2115 | −1.6375 | −1.5708 | 0.0667 | 2.2793 | 0.3271 |
| DF | AH | −5.6311 | −5.4202 | −1.6356 | −1.5801 | 0.0555 | 2.3300 | 0.4359 |
| DF | DH | −5.4260 | −4.9707 | −1.6312 | −1.5385 | 0.0928 | 2.2597 | 0.2537 |
| DF | DH | −5.4260 | −4.9707 | −1.6312 | −1.5385 | 0.0928 | 2.2597 | 0.2537 |
| DA | AC | −5.5310 | −5.2129 | −1.6228 | −1.5785 | 0.0444 | 2.3004 | 0.4929 |
| AH | AH | −5.9010 | −5.3819 | −1.6166 | −1.5197 | 0.0969 | 2.5217 | 0.4130 |
| DA | DG | −5.5481 | −5.1993 | −1.6152 | −1.5746 | 0.0405 | 2.2858 | 0.4130 |
| DA | AA | −5.5391 | −5.2042 | −1.6122 | −1.5559 | 0.0563 | 2.3003 | 0.4145 |
| DA | DF | −5.5391 | −5.1890 | −1.5970 | −1.5453 | 0.0517 | 2.2855 | 0.3665 |
| DA | DB | −5.4020 | −5.1601 | −1.5942 | −1.5507 | 0.0435 | 2.2787 | 0.4239 |
| DA | DA | −5.3642 | −5.1253 | −1.5333 | −1.4612 | 0.0721 | 2.2783 | 0.3127 |
| DH | DH | −4.9294 | −4.7770 | −1.5107 | −1.4307 | 0.0800 | 2.2237 | 0.2698 |

EXAMPLE 3: FABRICATION AND TESTING OF OLED

All organic materials were purified by sublimation before deposition. OLEDs were fabricated onto an ITO coated glass substrate that served as the anode, and topped with an aluminum cathode. All organic layers were thermally deposited by physical vapor deposition, in a vacuum chamber with a base pressure of <$10^{-7}$ torr.

Each cell, containing HIL1, HIL2, HTL, EML host, EML dopant, ETL, or EIL, was placed inside a vacuum chamber, until it reached $10^{-6}$ torr. To evaporate each material, a controlled current was applied to the cell, containing the material, to raise the temperature of the cell. An adequate temperature was applied to keep the evaporation rate of the materials constant throughout the evaporation process.

For the HIL1 layer, N4,N4'-diphenyl-N4,N4'-bis(9-phenyl-9H-carbazol-3-yl)-[1,1'-biphenyl]-4,4'-diamine was evaporated, until the thickness of the layer reached 60 nm. Next, for the HIL2 layer, dipyrazino[2,3-f:2',3'-h]quinoxaline-2,3,6,7,10,11-hexacarbonitrile was evaporated, until the thickness reached 5 nm. For the HTL layer, N-([1,1'-biphenyl]-4-yl)-9,9-dimethyl-N-(4-(9-phenyl-9H-carbazol-3-yl)phenyl)-9H-fluoren-2-amine was evaporated, until the thickness reached 25 nm. For the EML layer, 9-phenyl-10-(4-phenylnaphthalen-1-yl)anthracene (BH-1, host) and N1,N6-bis(5'-fluoro-[1,1':3',1''-terphenyl]-4'-yl)-N1,N6-diphenylpyrene-1,6-diamine (BD-1, dopant) were co-evaporated, until the thickness reached 20 nm. The doping ratio for the dopant material was 2 wt %. For the ETL layer, the ETL compounds were co-evaporated with lithium quinolate (Liq), until the thickness reached 30 nm with evaporation ratio of 1:1. Finally, "2 nm" of a thin electron injection layer (Liq) was evaporated. See Table 2.

For the inventive example, the above procedure was followed, and the ETL was Ex. 1 described above. For the comparative example, the above procedures was followed, and the ETL was 2,4-bis(9,9-dimethyl-9H-fluoren-2-yl)-6-(naphthalen-2-yl)-1,3,5-triazine (Comparative ETL-1).

The current density-voltage-luminance (J-V-L) characterizations for the OLED devices were performed with a source measurement unit (KEITHLY 2635A) and a luminescence meter (MINOLTA CS-100A). Electroluminescence (EL) spectra of the OLED devices were collected by a calibrated CCD spectrograph. Color is reported using the CIE system, reporting the X and Y coordinates.

TABLE 2

Device Materials

| | Name |
|---|---|
| Hole Injection Material 1 | N4,N4'-diphenyl-N4,N4'-bis(9-phenyl-9H-carbazol-3-yl)-[1,1'-biphenyl]-4,4'-diamine |
| Hole Injection Material 2 | dipyrazino[2,3-f:2',3'-h]quinoxaline-2,3,6,7,10,11-hexacarbonitrile |
| Hole Transporting Material | N-([1,1'-biphenyl]-4-yl)-9,9-dimethyl-N-(4-(9-phenyl-9H-carbazol-3-yl)phenyl)-9H-fluoren-2-amine |
| Fl Blue Host | 9-phenyl-10-(4-phenylnaphthalen-1-yl)anthracene |
| Fl Blue Dopant | N1,N6-bis(5'-fluoro-[1,1':3',1''-terphenyl]-4'-yl)-N1,N6-diphenylpyrene-1,6-diamine |
| Comparative ETL-1 | 2,4-bis(9,9-dimethyl-9H-fluoren-2-yl)-6-(naphthalen-2-yl)-1,3,5-triazine |
| Electron Injection Material | lithium quinolate |

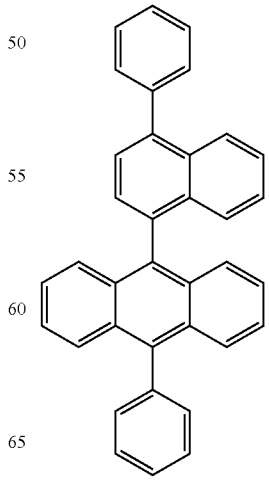

BH-1

-continued

ETL-1

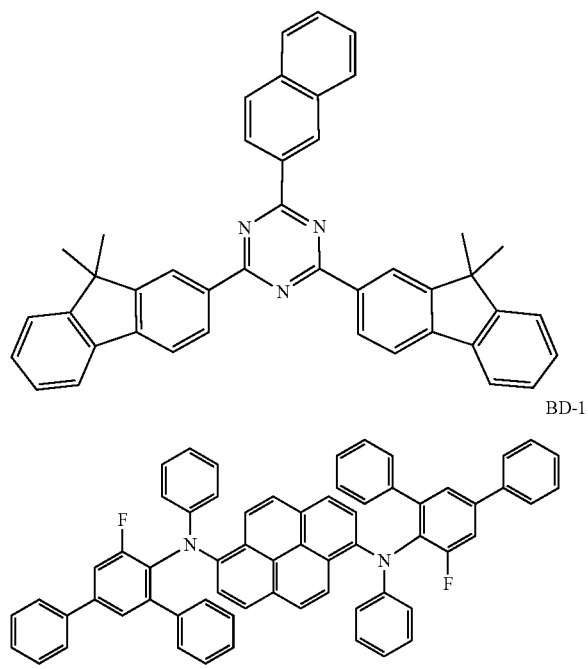

BD-1

ETL-1 is a comparative compound. Ex. 1, as described above, is an example of the composition of the present invention, having structure (I) with R1=DC) and R2=AE).

Results of testing the OLED devices were as follows:

TABLE 3

Device results

| | | Voltage @1000 nit [V] | Luminous Efficiency @1000 nit [Cd/A] | CIE (X, Y) |
|---|---|---|---|---|
| Comparative | ETL-1: Liq | 4.5 | 4.7 | 0.139, 0.088 |
| Inventive | Ex. 1: Liq | 4.2 | 5.9 | 0.139, 0.089 |

The inventive OLED device had color and voltage comparable to those of the comparative OLED device, and the inventive OLED device had superior luminous efficiency.

EXAMPLE 5: GLASS TRANSITION TEMPERATURE

The Tg of Ex. 1 was measured as described above. Tg was 143° C.

The invention claimed is:

1. A composition comprising one or more phenanthroquinazoline-core compounds having structure (I)

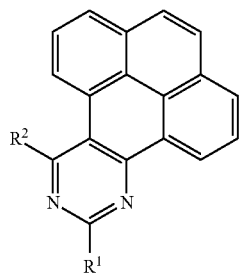

(I)

wherein each of $R^1$ and $R^2$ is independently a substituted or unsubstituted phenyl group.

2. The composition of claim 1 wherein $R^1$ is

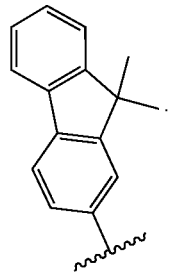 [SMILES: *c1ccc2c(c1)C(C)(C)c1ccccc1-2]

3. The composition of claim 1 wherein $R^2$ is

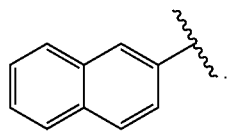

4. The composition of claim 1 wherein the compound having structure (I) has LUMO of −1.5 eV to −1.9 eV.

5. The composition of claim 1 wherein the compound having structure (I) has Tg of 90° C. to 200° C.

6. An organic light-emitting diode comprising an emitting layer and an electron transport layer, wherein the electron transport layer comprises the composition of claim 1.

* * * * *